(12) United States Patent
Hodges et al.

(10) Patent No.: US 6,541,007 B1
(45) Date of Patent: Apr. 1, 2003

(54) **VACCINE FOR *PSEUDOMONAS AERUGINOSA***

(75) Inventors: Robert S. Hodges, Edmonton (CA); Randall T. Irvin, Sherwood Park (CA); Paul J. Cachia, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/345,624

(22) Filed: Jun. 30, 1999

Related U.S. Application Data

(63) Continuation of application No. 09/306,241, filed on May 6, 1999, now abandoned.
(60) Provisional application No. 60/084,444, filed on May 6, 1998.

(51) Int. Cl.⁷ .................. A61K 39/385; A61K 39/02; A61K 39/108; A61K 39/00; C07K 2/00
(52) U.S. Cl. .................. 424/197.11; 424/193.1; 424/190.1; 424/184.1; 424/260.1; 424/234.1; 424/185.1; 530/300; 530/825; 530/806; 530/807

(58) Field of Search .................. 424/190.1, 184.1, 424/193.1, 197.11, 203.1, 234.1, 260.1, 242.1; 514/2; 530/300, 825, 820, 326, 806, 807

(56) References Cited

PUBLICATIONS

Sheth et al. Biomedical Peptides, Proteins & Nucleic Acids 1: 141–148, 1995.*

* cited by examiner

*Primary Examiner*—S. Devi
(74) *Attorney, Agent, or Firm*—Bell, Boyd & Lloyd LLC

(57) ABSTRACT

A C-terminal pilin peptide vaccine for immunizing or treating a patient for infection by a *Pseudomonas aeruginosa* (PA) infection is disclosed. The peptide comprises the peptide identified as SEQ ID NOS. 3–6; and a carrier protein conjugated to the peptide. Also disclosed is a pilin peptide C-terminal PA pilin peptide having the amino acid sequence identified as SEQ ID NO:3, and analogs thereof having one of residues T, K, or A at position 130, D, T, or N at position 132, Q, A, or V at position 133, E, P, N, or A at position 135, Q, M, or K at position 136, and I, T, L, or R at position 138, excluding SEQ ID NOS: 1, 2, 9, 10, and 11, and the ability to cross-react with antibodies against the corresponding C-terminal peptides from PA strains PAK and PAO.

1 Claim, 12 Drawing Sheets

```
PAK     Ac  K  C [T] S [D] Q  D [E][Q] F [I] P  K  G  C  S  K  OH
PAO     Ac  A  C [K] S [T] Q  D [P][M] F [T] P  K  G  C  D  N  OH

TBOU1  -C-S-I-S-S-T-P-A-N-W-K-P-N-Y-A-P-S-N-C-
```

Fig. 10

VACCINE FOR *PSEUDOMONAS AERUGINOSA*

The present application is a continuation of U.S. patent application Ser. No. 09/306,241 filed on May 6, 1999, now abandoned, which claimed domestic priority to U.S. Provisional Patent Application No. 60/084,444 filed on May 6, 1998, which are herein incorporated by reference.

FIELD OF THE INVENTION

The present invention relates to a vaccine for *Pseudomonas aeruginosa*, and in particular to novel vaccine peptides.

REFERENCES

1. Irvin, R. T., "Attachment and colonization of *Pseudomonas aeruginosa*: Role of the surface structures", in *Pseudomonas aeruginosa as an Opportunistic Pathogen*, (Campa, M., M. Bendinelli, and H. Friedman, Eds.), pp 19–42, Plenum Press, New York (1993).
2. Pier, G. B., *J. Infect. Dis.* 151:575–580 (1985).
3. Rivera, M. and Nicotra, M. B., *Am. Rev. Respir. Dis.* 126:833–836 (1982).
4. Todd, T. R. J., et al., *Am. Rev. Respir. Dis.* 140:1585–1589 (1989).
5. Irvin, R. T., et al., *Infect. Immun.* 57:3720–3726 (1989).
6. Lee, K. K., et al., *Mol. Microbiol.* 3:1493–1499 (1989).
7. Doig, P., et al., *Infect. Immun.* 55:1517–1522 (1987).
8. McEachran, D. and Irvin, R. T., *Can. J. Microbiol.* 31:563–569 (1985).
9. Irvin, R. T., et al., *Microb. Ecol. Health Dis.* 3:39–47 (1990).
10. Bradley, D. E., *Genet. Res.* 19:39–51 (1972).
11. Folkhard, W. F., et al., *J. Mol. Biol.* 149:79–93 (1981).
12. Paranchych, W., et al., *Clin. Invest. Med.* 9:113–118 (1986).
13. Paranchych, W., et al., "Expression, processing, and assembly of *Pseudomonas aeruginosa* N-methylphenylalanine pilin", in *Pseudomonas: Biotransformations, Pathogenesis and Evolving Biotechnology*, (Sliver, S., et al., Eds.), pp 343–351, American Society for Microbiology, Washington, D.C. (1990).
14. Pasloske, B. L., et al., *J. Bacteriol.* 170:3738–3741 (1988).
15. Yu, L., et al., *Infect. Immun.* 62:5213–9 (1994).
16. Sheth, H. B., et al., *Mol. Microbiol.* 11:715–23 (1994).
17. Doig, P., et al., *Infect. Immun.* 58:124–130 (1990).
18. Lee, K. K., *Infect. Immun.* 57:520–526 (1989).
19. Sheth, H. B., et al., *Biomed. Pept. Proteins and Nucleic Acids* 1:141–148 (1995).
20. Hanessian, S., et al., *Nature (London)* 229:209–210 (1971).
21. Jones, R. J., et al., *Lancet* ii:401–403 (1978).
22. MacIntyre, S., et al., *Infect. Immun.* 52 (1986).
23. Pier, G. B. and Thomas, D. M., *J. Infect. Dis.* 148:206–213 (1983).
24. Cryz, S. J., et al., *Antibiot. Chemother.* 42:177–183 (1989).
25. Lam, J. S., , et al., *Infect. Immun.* 42:88–98 (1983).
26. Matthews-Greer, J. M. and Gilleland, Jr., H. E., *J. Infect. Dis.* 155:1281–1291 (1987).
27. Pier, G. B., et al., *Science* 249:537–540 (1990).
28. Holder, I. A. and Naglich, J. G., *J. Trauma.* 26:118–122 (1986).
29. Rotering, H. and Dorner, F., *Antibiot. Chemother.* 42:218–228 (1989).
30. Sezen, I. Y., et al., *Zentralbl. Bakteriol. Hyg. I. Abt. Orig.* 231:126–132 (1975).
31. Cryz, S. J., Jr., et al., *Infect. Immun.* 39:1072–1079 (1983).
32. Lydick, E., et al., *J. Infect. Dis.* 151:375 (1985).
33. Finke, M., et al., *Infect. Immun.* 59:1251–1254 (1991).
34. Taussig, M. J., "Antigenic competition", in *The Antigens* (Sela, M., Ed.), pp 333–368, Academic Press, New York (1977).
35. Hunt, J. D., et al., *Vaccine* 13:1649–1657 (1995).
36. Hunt, J. D., et al., *Immunol. Cell Biol.* 74:81–89 (1996).
37. Campbell, A. P., et al., *Biochemistry* 34:16255–16268 (1995).
38. Campbell, A. P., et al., *J. Mol. Biol.* 267:382–402 (1997).
39. McInnes, C., et al., *Biochemistry* 32:13432–40 (1993).
40. Rudner, X. L., et al., *Invest. Ophthalmol. Vis. Sci.* 33:2185–93 (1992).
41. Lee, K.K., et al., *Infect. Immun.* 58:2727–2732 (1990).
42. Wong, W. Y., Ph.D. Thesis: "Synthetic Peptide Approaches to Study the Adherence Binding Domain of the Pilin Protein of *Pseudomonas aeruginosa* Strain PAK," University of Alberta, Edmonton, Alberta, Canada, p. 222 (1994).
43. Wong, W. Y., et al., "Pseudomonas Pilin Vaccine," in The 8th Annual North American Cystic Fibrosis Conference, Orlando, Fla. (1994).
44. Wong, W. Y., et al., *Protein Sci.* 1:1308–18 (1992).
45. Campbell, A. P., et al., *Int. J. Pept. Protein Res.* 48:539–552 (1996).
46. Wong, W. Y., et al., *Biochemistry* 34:12963–12972 (1995).
47. Paranchych, W., et al., *Can. J. Microbiol.* 25:1175–1181 (1979).
48. Erickson, B. W. and Merrifield, R. B., "Solid-phase peptide synthesis", in The Proteins, (Neurath, H. and R. L. Hill, Eds.), pp 255–527, Academic Press, New York (1976).
49. Nieto, A., et al., *Mol. Immunol.* 21:537–543 (1984).

BACKGROUND OF THE INVENTION

*Pseudomonas aeruginosa* is a serious opportunistic gram-negative bacterial pathogen which can cause fatal infections in immunocompromised and immunosuppressed patients [1–4]. The first step in the infection process is the attachment to the host cell. This attachment is mediated by pili on the surface of the bacterium [2, 5, 6]. *P. aeruginosa* uses several adhesins to mediate attachment to mucosal surfaces, but analysis of the binding properties of the adhesins [1, 7, 8] and binding competition studies [9] indicate that the pilus is the dominant adhesin responsible for initiating infections [1].

*P. aeruginosa* pili are polarly located, with a structure resembling a hollow tube of 5.2 nm in outer diameter, 1.2 nm in central channel diameter, and an average length of 2.5 μm [10–12]. The pilus of *P. aeruginosa* is composed of multiple copies of a 13–17 kDa monomeric protein subunit called pilin. The C-terminal region of the pilin monomer contains the epithelial cell binding domain [5, 12] and is semiconserved in seven different strains of this bacterium [13, 14]. This semiconserved region has also been shown to bind to a minimal structural carbohydrate receptor sequence, β-GalNAc(1–4)βGal, found in glycosphingolipids, specifically asialo-GM1 and asialo-GM2 [15, 16]. Furthermore, the C-terminal disulfide-bridged 17-residue region of the PAK pilin is known to be important in raising antibodies that block binding of both bacteria or their pili to epithelial cells [6, 17, 18]. Both monoclonal antisera generated from *P.*

*aeruginosa* pili or polyclonal antisera generated from synthetic peptides representing the receptor binding domain of the pathogen have been shown to be efficacious in preventing infection [19].

Different types of *Pseudomonas aeruginosa* immunogens have been tried or are under development as vaccines. These include lipopolysaccharides [20–22], polysaccharide [23], polysaccharide conjugate [24], outer-membrane protein [25, 26], mucoid exopolysaccharide [27], flagella [28, 29], protease [30], elastase [31], exotoxin A [31, 32], and lipoprotein I [33]. An alternate to these approaches to vaccination against *P. aeruginosa* could employ a multivalent pili vaccine. However, a potential problem exists in this approach: inhibition of the immune response to one antigen or determinant by the administration of another antigen or determinant. This phenomenon, termed antigenic competition [34], leads to the reduction of antibody production and has been shown to occur between chemically related and unrelated antigens and also between associated and non-associated antigenic determinants. An example of this type of competition has been reported by Hunt and coworkers [35, 36] in the development of a multivalent pili vaccine against ovine footrot. In this case, antigenic competition occurs between the nine pili serotypes of the bacterium *Dichelobacter nodosus* that are required in a vaccine for complete protection against the disease. These results suggested that a cocktail or multicomponent vaccine composed of synthetic peptide immunogens representing the known strains of *Pseudomonas aeruginosa* pili may be problematic.

SUMMARY OF THE INVENTION

The invention includes a peptide vaccine for immunizing or treating a patient for infection by a *Pseudomonas aeruginosa* (PA) infection. The invention comprises (i) the peptide identified as SEQ ID NOS. 3–6; and (ii) a carrier protein conjugated to the peptide.

The peptide vaccine is useful in protecting a subject against Pseudomonas infection, by administering the vaccine to the subject, also in accordance with the invention.

In another aspect, the invention includes a C-terminal PA pilin peptide having the amino acid sequence identified as SEQ ID NO: 3, and analogs thereof having one of residues T, K, or A at position 130, D, T, or N at position 132, Q, A, or V at position 133, E, P, N, or A at position 135, Q, M, or K at position 136, and I, T, L, or R at position 138, excluding SEQ ID NOS: 1, 2, 9, 10, and 11. The claimed peptide is also characterized by its ability to cross-react with antibodies against the corresponding C-terminal peptides from PA strains PAK and PAO, preferably also against antibodies specific against a C-terminal peptide from PA strains CD4, K122, or KB7.

In still another aspect, the invention includes a method of selecting a peptide for use in a vaccine against *Pseudomonas aeruginosa*. The method includes the steps of (i) constructing a library of 1296 C-terminal peptides having the amino acid sequence identified as SEQ ID NO: 3, and analogs thereof having one of residues T, K, or A at position 130, D, T, or N at position 132, Q, A, or V at position 133, E, P, N, or A at position 135, Q, M, or K at position 136, and I, T, L, or R at position 138, and (ii) selecting library members which are cross-reactive with cross-react with antibodies against the corresponding C-terminal peptides from PA strains PAK, PAO.

These and other objects and features of the invention will become more fully apparent when the following detailed description of the invention is read in conjunction with the accompanying drawings.

BRIEF DESCRIPTION OF THE DRAWINGS

FIG. 1 shows the native sequences PAK (SEQ ID NO: 1) and PAO (SEQ ID NO:2), and the sequences of six PAK-peptide analogs, identified as CS1 (SEQ ID NO:3); CS2 (SEQ ID NO:4); CS3 (SEQ ID NO:5); CS4 (SEQ ID NO:6); E135A (SEQ ID NO: 7); and E135P (SEQ ID NO: 8), where the amino acid variations with the PAK-peptide sequence in the six analogs are indicated by circles;

FIG. 10 shows the sequences of the C-terminal cell surface binding domains of three PA strains P1, 492C, and TBOU1;

DETAILED DESCRIPTION OF THE INVENTION

Overview of Results

Initially, the cross-reactivity of the native sequence PAK (FIG. 1; SEQ ID NO:1) when it was used as immunogens in rabbits was examined. Polyclonal serum from this immunogen was studied using competition ELISA. The results demonstrated that this antiserum was cross-reactive with the native PAO sequence (SEQ ID NO:2) in the presence of native PAK sequence on plates coated with PAK strain pili. This cross-reactivity did not extend to other strains tested (i.e. KB7 and P1).

Initially, position 135 in the PAK sequence was chosen as a mutation site for increasing cross-reactivity, and proline from the homologous position in the native PAO sequence was used at position 135 in the native PAK backbone (FIG. 1, E135P, SEQ ID NO: 8). Competition results indicated that the antiserum raised to this immunogen was less cross-reactive than native PAK antiserum and was not cross-reactive with any of the other strains tested (i.e. KB7 and P1).

A second single mutant sequence was also constructed which contained alanine at position 135 (FIG. 1; E135A, SEQ ID NO: 7). This mutant contained the homologous residue, alanine, from position 135 in strain KB7 at position 135 in the PAK backbone. This sequence was found to generate antiserum which was as cross-reactive as native PAK sequence with PAO. Furthermore, this cross-reactivity was more broadly based than that of native PAK sequence; cross-reactivity was found against strains PAO, KB7 and P1. In PAOwt challenge experiments (FIG. 2), E135A immunization demonstrated enhanced survival time in a mouse model.

A double mutant (FIG. 1; CS2, SEQ ID NO:4) (D132T, E135P)) was also synthesized. Results obtained from competition ELISA demonstrate that polyclonal antiserum raised in rabbits to the double mutant had enhanced cross-reactivity to PAO over that demonstrated by PAK. Furthermore, PAOwt challenge experiments demonstrated (FIG. 3) complete protection against challenge with PAOwt.

Figure 2:
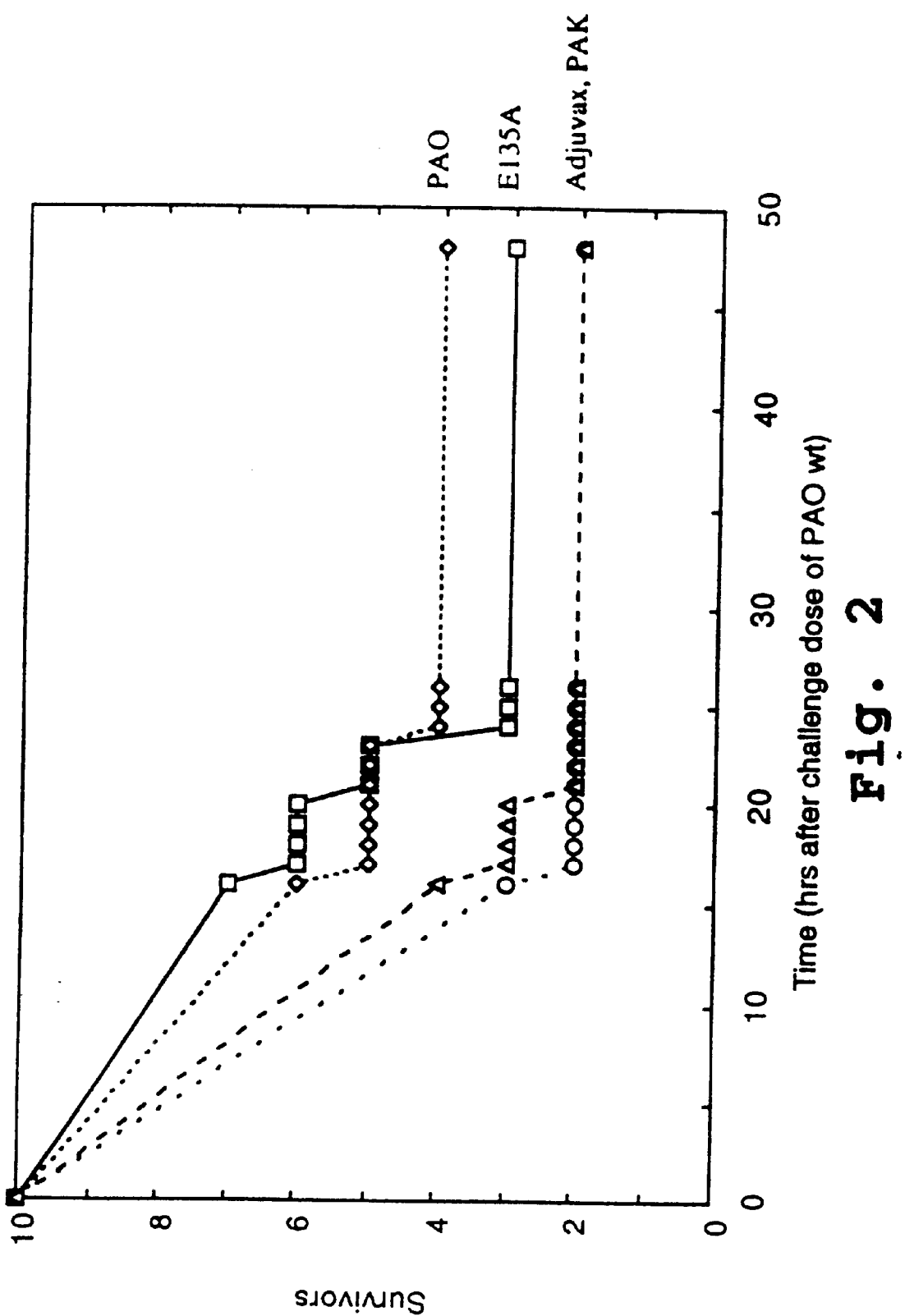
FIG. 2 shows survival times of animals immunized with the E135A antigen (SEQ ID NO: 7), after challenge with PAOwt.
Figure 3:
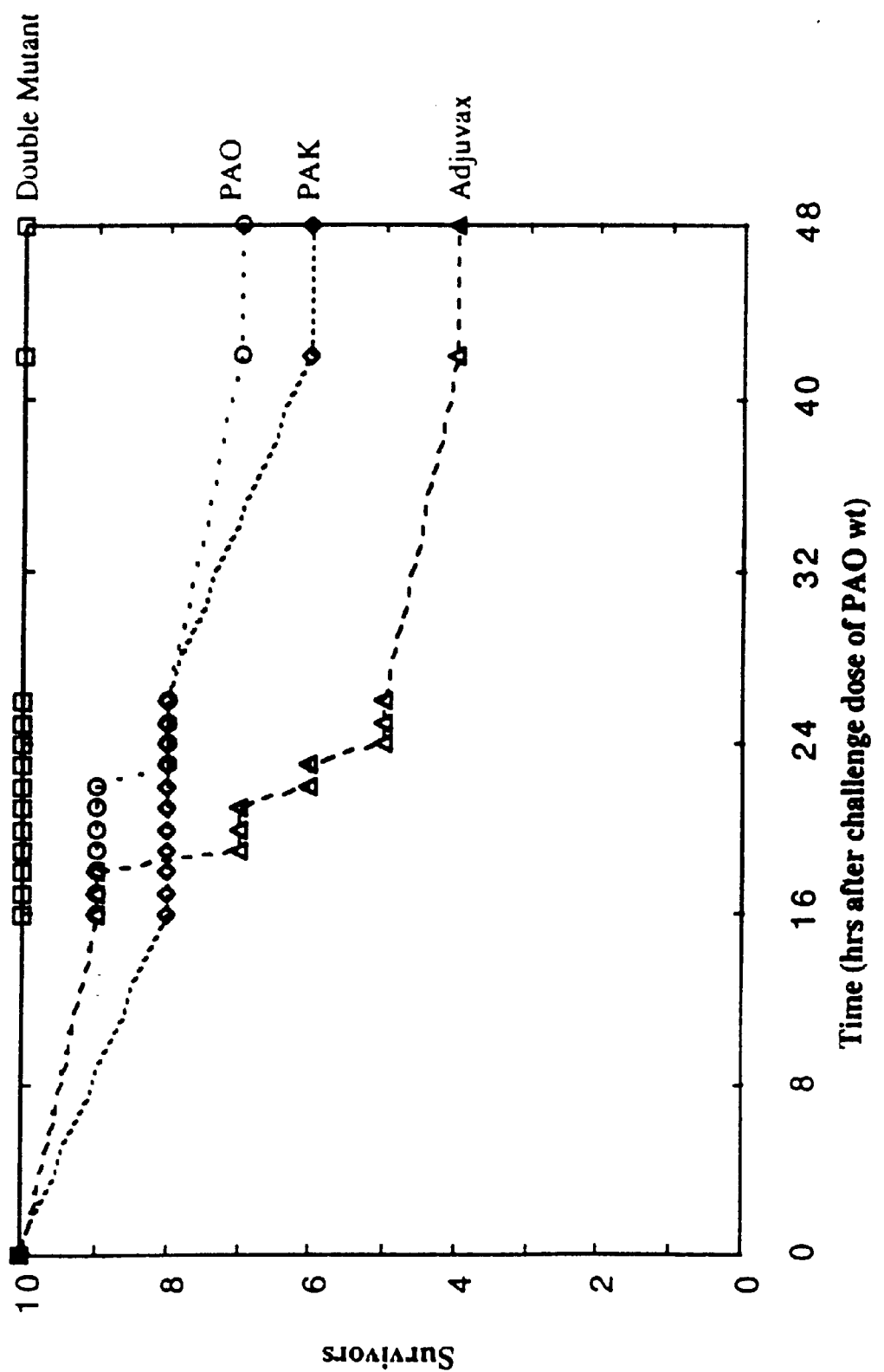
FIG. 3 shows survival times of animals immunized with the CS2 (double mutant) (SEQ ID NO: 4), PAO (SE ID NO:2) or PAK (SEQ ID NO:1) peptide, after challenge with PAOwt.

FIG. 1 shows the native sequences PAK and PAO (residues 128–144), the single mutant sequences E135A, E135P and the multiple mutations indicated as CS1 (SEQ ID NO:3, CS2 (SEQ ID NO:4, CS3 (SEQ ID NO:5), and CS4 (SEQ ID NO:6). The figure is designed to highlight the differences between the various sequences (boxed residues). For instance, there are eight differences between the native sequences PAK and PAO. There is only one difference between PAK and E135A and eight differences between E135A and PAO, yet the peptide E135A generates antiserum which shows enhanced cross-reactivity to PAO and enhanced survival time in challenge from PAOwt (FIG. 2). In contrast, E135P has seven differences compared to PAO and only one difference compared to PAK, yet the peptide generates antiserum which is strain specific for PAK and is less cross-reactive to PAO than PAK peptide. The double mutant CS2 has six differences with respect to PAO and two differences with respect to PAK. The antiserum provides complete protection to challenge from PAOwt (FIG. 3).

Figure 4:
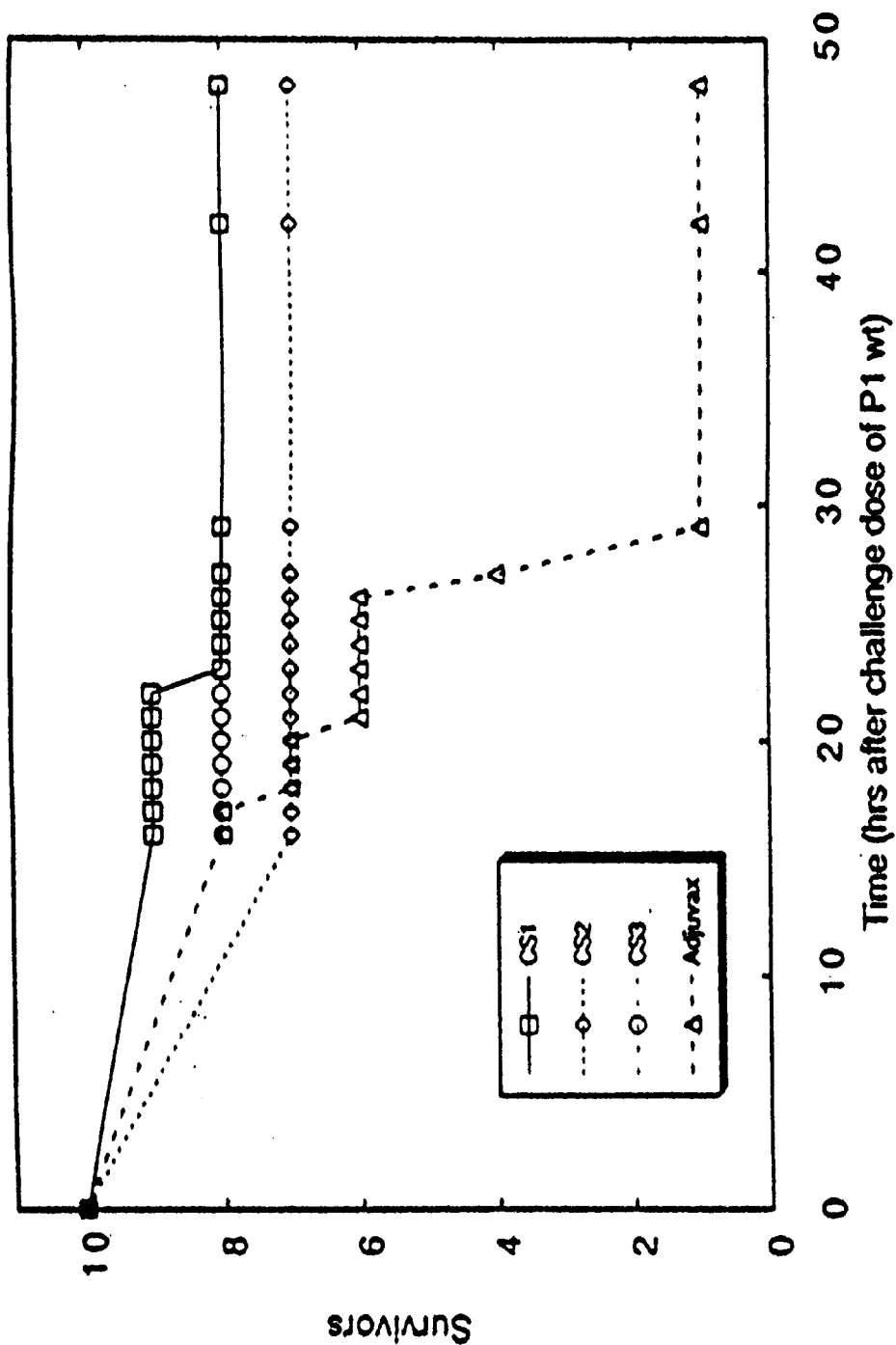
FIG. 4 shows survival times of animals immunized with the CS1 (SEQ ID NO: 3), CS2 (SEQ ID NO:4), or CS3 (SEQ ID NO:5) peptide, after challenge with P1wt.
Figure 5:
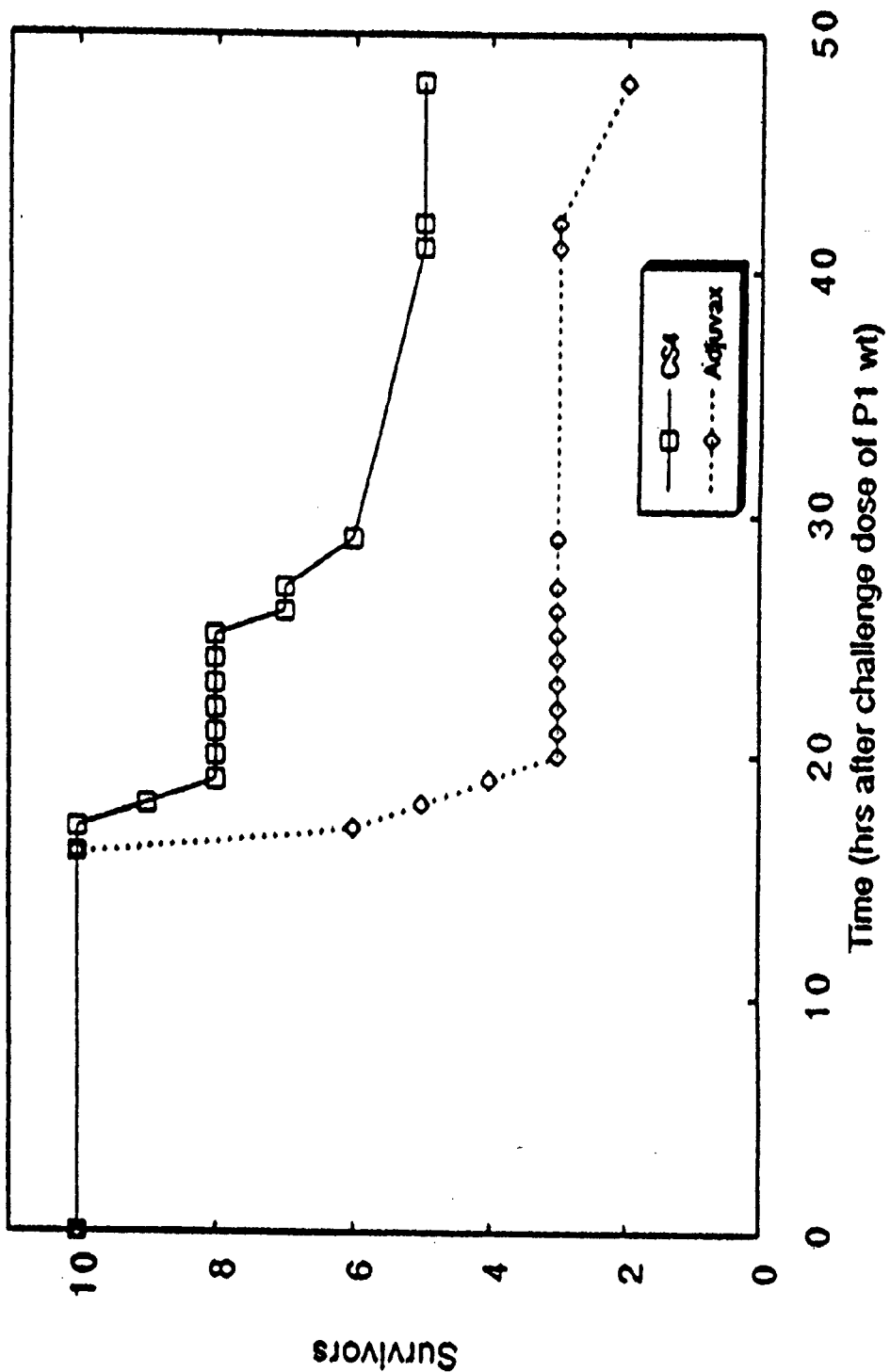
FIG. 5 shows survival times of animals immunized with the CS4 (SEQ ID NO: 6) peptide, after challenge with P1wt.
Figure 6:
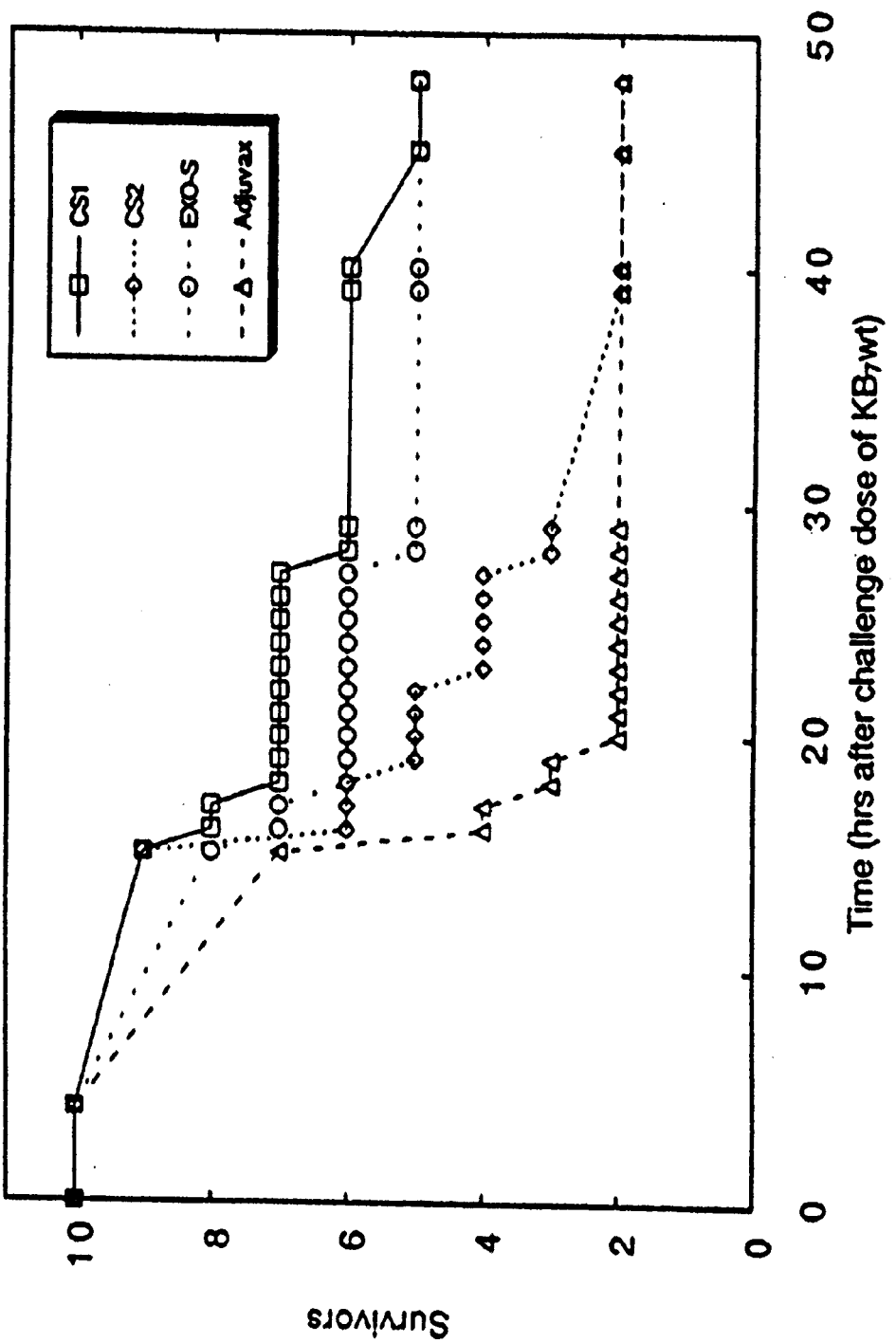
FIG. 6 shows survival times of animals immunized with the CS1 (SEQ ID NO: 3), CS2 (SEQ ID NO:4), or EXO-S peptide, after challenge with $KB_7$.
Figure 7:
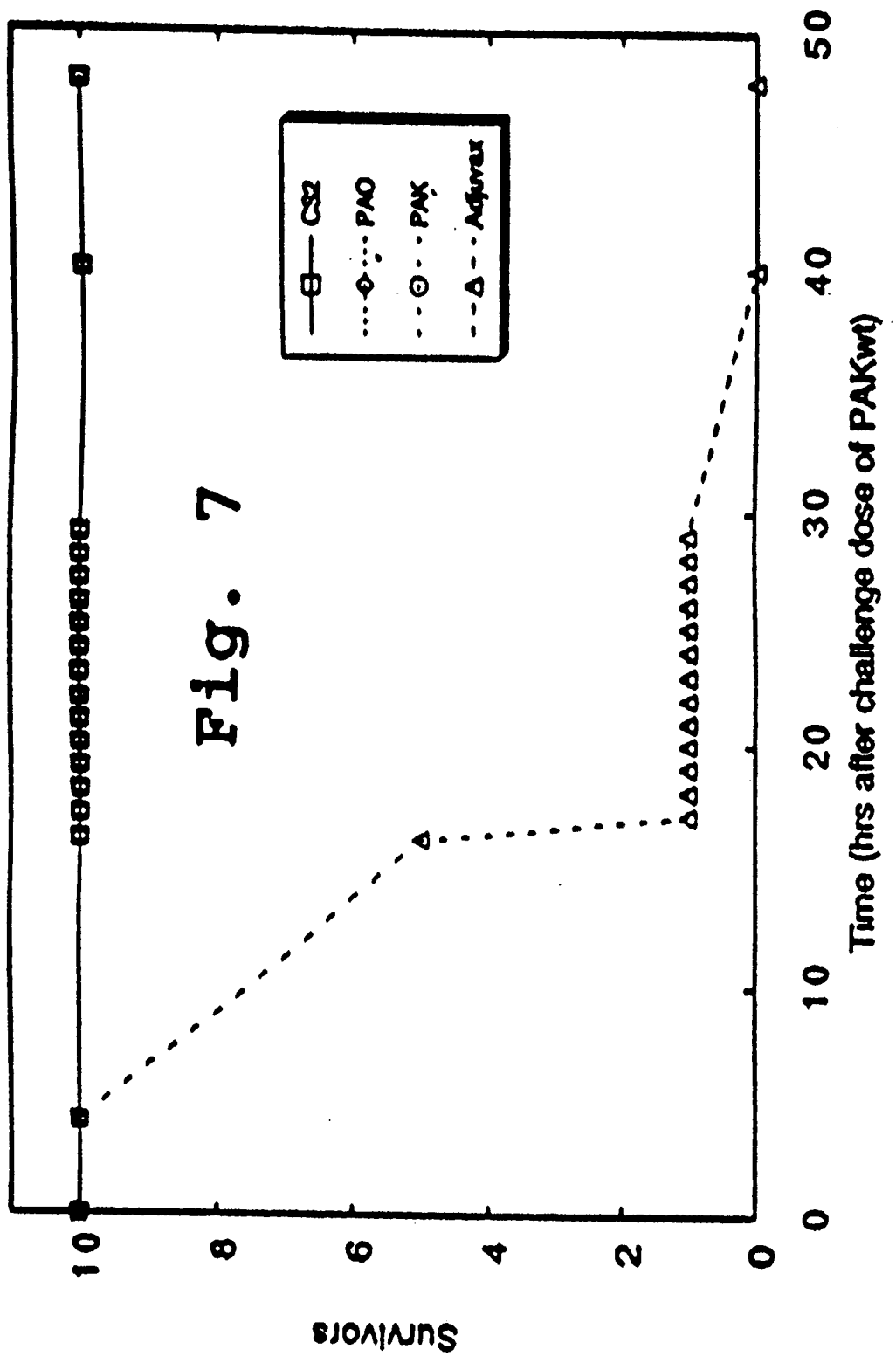
FIG. 7 shows survival times of animals immunized with the with the CS2 (SEQ ID NO: 4), PAO (SE ID NO:2) or PAK (SEQ ID NO:1) peptide, after challenge with PAKwt.

Similar vaccination methods demonstrated that CS1, CS2, and CS3 all provided a high level of protection against infection in animals challenged with P1 (FIG. 4); that CS4 provided good protection against animals also challenged with P1 (FIG. 5); that CS1 provided good protection against infection in animals challenged with $KB_7$ (FIG. 6); and that CS2 provided a very high level of protection in animals challenged with PAK.

Figure 9:
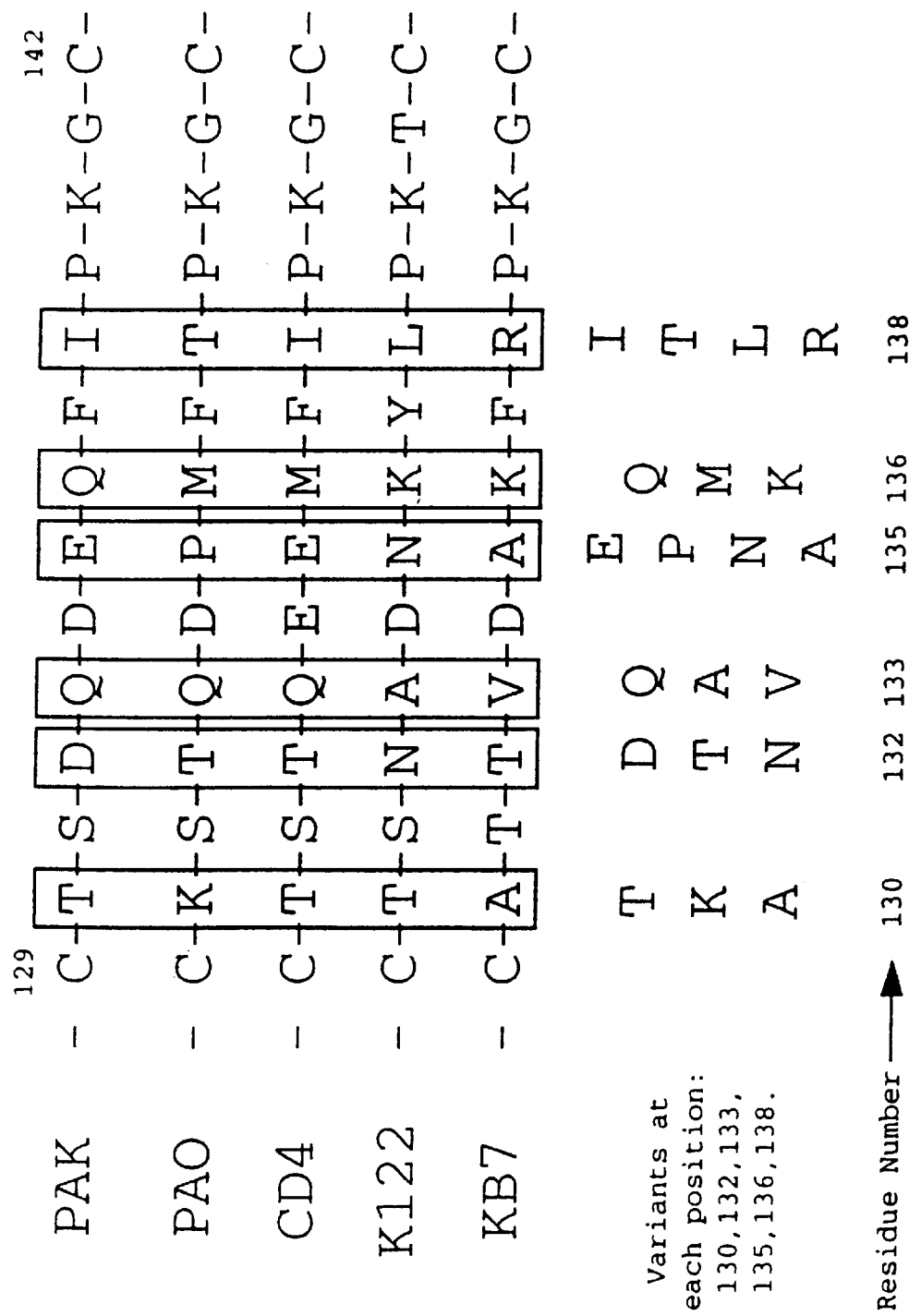
FIG. 9 shows consensus and amino acid variations among in the C-terminal region peptides in five strains of PA.
Figure 11:
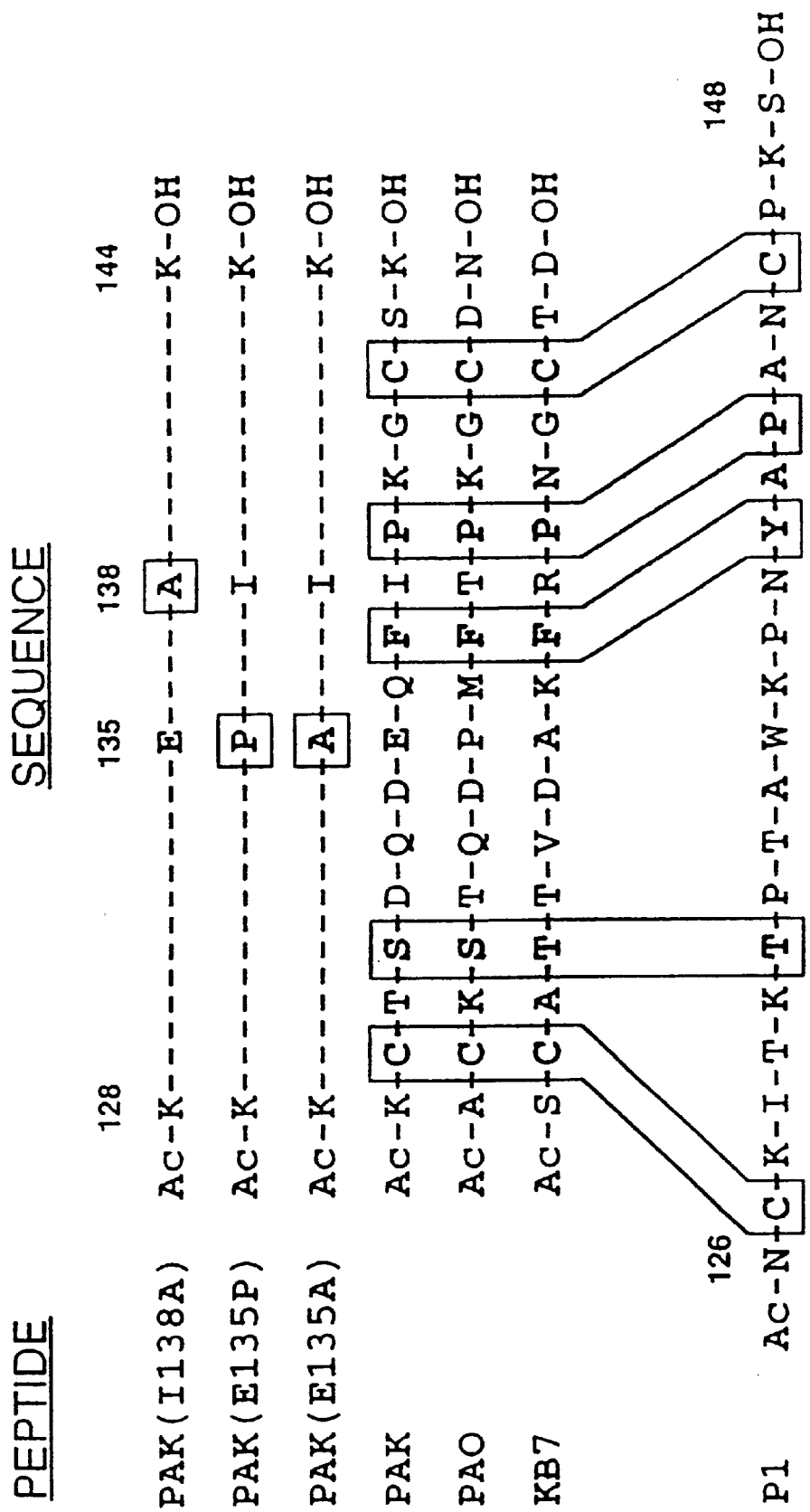
FIG. 11 shows the sequences of the C-terminal cell surface binding domains of four *Pseudomonas aeruginosa* pilin strains PAK, PAO, KB7 and P1 together with the sequences of three PAK analogues I138A, E135P and E135A.

FIG. 9 describes 5 sequences of the C-terminal peptides from *P. aeruginosa*. These sequences from the protein Pilin encompass the binding domain responsible for attachment to the host cell surface receptors. The peptides are 14-residues in length and contain disulfide-bridges between the cysteine residues at positions 129 and 142. The boxed regions define homologous positions in the 5 sequences which are the most variable in amino acid composition and contain 3 to 4 different amino acid variants across the 5 strains (see FIG. 9 positions 130, 132, 133, 135, 136 and 138). Other positions in these sequences contain the same amino acid in a position (i.e. position 139 contains proline) or have only 1 amino acid different across the 5 strains (i.e. position 137 contains the residues phenylalanine and tyrosine). The peptide library containing all possible variants of the PAK sequence in the boxed positions would contain 1296 (3×3×3×4×3×4) peptides including the native PAK sequence itself, excluding any residues in these 6 positions that are not found in the five strains. Two of these sequences, the single mutant E135A and the multiple mutants CS1, CS2, CS3, and CS4 provide cross-protection against various *P. aeruginosa* strains challenged in the mouse model (FIGS. 2–7). The emphasis has been on residues between the positions 129 and 142 because, to date, all epitopes that have been mapped, in both polyclonal and monoclonal antibodies raised to larger C-terminal fragments containing this region, show that the epitopes lie within the loop structure.

FIG. 10 contains the sequences of 3 other native PA C-terminal sequences (P1, SEQ ID NO: 12, 492C, SEQ ID NO: 13, and TBOU1 (SEQ ID NO: 14) that contain larger loops than the 5 shown in FIG. 9. Complete protection will only be achieved if mutant sequence(s) should cross-react with these sequences.

Detailed Studies

Previously, native polyclonal antisera (17-O1), raised against the native PAK C-terminal pilin synthetic sequence containing the intrachain disulfide bridge (AcPAK (128–144)OH) was shown to be cross-reactive with synthetic peptide (AcPAO (128–144)OH) and pilin from strain PAO [6, 18, 41], a result confirmed herein. Epitope mapping studies using single alanine substitution analogs of the PAK sequence were performed to determine the side-chain specificity of antisera raised to the reduced and disulfide-bridged (oxidized) immunogens.

The relative importance of each of the residues in the epitopic region is based on the analysis of the apparent binding constants (Ka). The Ka's at each position for both the native sequence ($K_N$) and the single alanine substitution analogue ($K_S$) are displayed as the ratio $K_N/K_S$ (Table 1).

The side-chains are divided into three types based on the $K_N/K_S$ ratios: critical, important and nonessential to antibody binding. A critical side-chain is one in which substitution by alanine decreases binding affinity more than 1,000-fold as compared to the native sequence. On the other hand, if the decrease in binding affinity is less than 10-fold, the side-chain is considered as nonessential. Side-chains whose contribution falls between these two extremes are defined as important. In antiserum 17-R1 the analysis reveals that the residues in positions 132, 134 to 136, 138 and 139 of oxidized AcPAK(128–144)OH are important to binding this native PAK peptide structure. Residue F137 is particularly critical for antibody binding as shown by the more than 10,000-fold decrease in binding affinity which occurs when phenylalanine is substituted by alanine in the native PAK sequence (Table 1; column, 17-R1; row, F137A). Antiserum 17-O1, raised to oxidized AcPAK(128–144)OH, has three residues at positions 134, 136 and 137 which are all classified as critical to antibody binding to native oxidized PAK peptide (Boxed residues; Table 1). In fact, antiserum raised to the analogue F137A, conjugated to Keyhole Limpet Haemocyanin, fails to bind native PAK pili indicating the importance of this side-chain, in the peptide immunogen, for maintaining recognition of the native pilin protein [42, 43]. Previous NMR studies on the conformation of the native immunogen showed that F137 is buried in the hydrophobic core of the folded peptide.

The position of F137 is critical for maintaining conformation of the immunogen and therefore critical to generating antiserum that recognizes the native sequence [39]. Furthermore, D134A and Q136A peptides bind to the two antisera 17-R1 and 17-O1 with dramatically different affinities (D134A binds 10-fold weaker to antiserum 17-R1 but 1600-fold weaker to antiserum 17-O1 and Q136A binds 390-fold weaker to antiserum 17-R1 compared to 3200-fold weaker to antiserum 17-O1 relative to the native PAK peptides). While positions 133 and 139 have maintained an important role in antibody binding ($10<K_N/K_S<1000$) in antiserum 17-O1, positions 132, 135 and 138 have become unimportant to antibody binding ($K_N/K_S<10$). This suggests that the oxidation of the peptide (formation of the disulfide bridge) in the immunogen results in a change in conformation that redefines residues critical to antibody binding to the native PAK peptide sequence. In other words, the disulfide bridge in the immunogen changes the side-chain specificity and enhances cross-reactivity of the resulting antisera (Table 1, $K_{PAK}/K_{PAO}$ ratios of antisera 17-R1 and 17-O1 are 4,400 vs 1,270, respectively).

Ideally, it is desired to have the cross-reactivity ratio between PAK and any other strain to approach unity. As a starting point, peptide antigens were constructed by substituting out side-chains important for strain-specificity but unimportant for cross-reactivity. For example, peptide E135A binds 480-fold weaker to strain-specific antiserum 17-R1 than the native peptide while E135A binds only 2-fold weaker to the more cross-reactive antiserum 17-O1. Thus, E135 seems important for strain-specificity but as the antiserum becomes more cross-reactive E135 becomes unimportant.

Initially, two peptide immunogens with single alanine substitutions at positions 135 and 138 were prepared. In addition, in order to specifically enhance cross-reactivity to strain PAO, a proline analogue at position 135 of the PAK sequence was synthesized. Proline was chosen because it is found in the corresponding position in the PAO native sequence. Since position E135 in the native PAK sequence was non-essential for binding to antiserum 17-O1, substitution of this residue by proline should enhance cross-reactivity of the antiserum prepared against the immunogen E135P.

The epitopes recognized by these antibodies prepared to the disulfide bridged peptides E135A, E135P and I138A were mapped by competitive ELISA assays using AcPAK (128–144)OH single alanine replacement analogs (Table 1; column, PEPTIDE) as competitive inhibitors in the presence of PAK native peptide on plates coated with PAK pili. The results of the substitution analyses show that the epitope (Table 1) recognized by each of these antisera spans the residues 132 to 140 in the native sequence AcPAK(128–144) OH similar to antisera 17-R1 and 17-O1 previously reported [43]. Analysis of the $K_N/K_S$ ratios, for each of these antisera, indicates that the importance of the individual residues has changed when compared to antiserum 17-O1. For example, dramatic changes occur in antisera I138A and E135P. In antiserum I138A the most critical residue for antigen binding is Q133. The previously critical residue in antiserum 17-O1, F137, is now unimportant to antigen binding. In antiserum E135P the residues critical for antigen binding are Q136 and K140. Similarly, the importance of F137 is dramatically reduced compared to antiserum 17-O1. Examination of the results for antiserum E135A reveals that deletion of the glutamic acid side-chain at position 135 and its replacement by the methyl group of alanine has not affected the antibodies affinity for this analogue ($K_N/K_S=1$) in comparison to the native PAK sequence. Therefore E135 is considered unimportant to antibody affinity. Furthermore, the analysis of cross-reactivity shows that the antiserum E135A exhibits similar cross-reaction with native PAO pilin sequence (Table 1; compare $K_{PAK}/K_{PAO}$ ratios for 17-O1 and E135A; 1,270 and 1,350, respectively).

Interestingly, the antiserum E135A has an increased affinity (~3-fold) for both PAK and PAO native peptide sequences (Table 2; row, E135A; columns, PAK and PAO; +3.2 and +3.0, respectively). As for other side-chain effects in the epitopic region, changes have occurred most noticeably in the $K_N/K_S$ values observed for positions Q133 (Table 1; column, E135A; row, Q133A). In antiserum E135A, the $K_N/K_S$ value has increased by a factor of 40-fold to a value of 830 in comparison to the value of 20 found in antiserum 17-O1.

The effect on residues Q136 and F137 are less pronounced yet remain large. The $K_N/K_S$ value for Q136 is reduced by a factor of approximately 6-fold while the value associated with F137 indicates a change however the precise magnitude is undetermined (Table 1; compare columns, 17-O1 and E135A; rows, Q136A; $K_N/K_S=3,200$ and 520 and F137A; $K_N/K_S=>10,000$ and >4,800, respectively). Q136 and F137 remain important and critical to binding. Analysis of residue D134 shows that the result of substitution of alanine at position 135 has had little effect on the critical nature of this side-chain (Table 1; compare columns, 17-O1 and E135A; row, D134A; $K_N/K_S=1,600$ and 1,200, respectively).

Finally, the result of the alanine substitution at position 135 has generally increased the importance of residues Q133, I138 and P139 to antiserum binding. The overall assessment of this substitution suggests that it has caused changes throughout the epitope which have decreased the contributions of some of the critical residues, namely Q136, but raised the contribution to antiserum binding of less critical but important residues, Q133, I138 and P139.

In summary, the results show that the epitopic region is similar in all the antisera 17-R1, 17-O1, E135A, I138A and E135P but side-chain specificities vary. These results demonstrate that it is possible to manipulate epitopic sequences by single amino acid mutation in the immunogen and retain binding affinity to the native antigen of the same order of magnitude as that of the native antiserum (Table 2; column PAK) and that the side-chain specificities observed are different in each of the antisera tested (Table 1).

Comparison of the Cross-Reactivity of the Different Antisera

Figure 12:
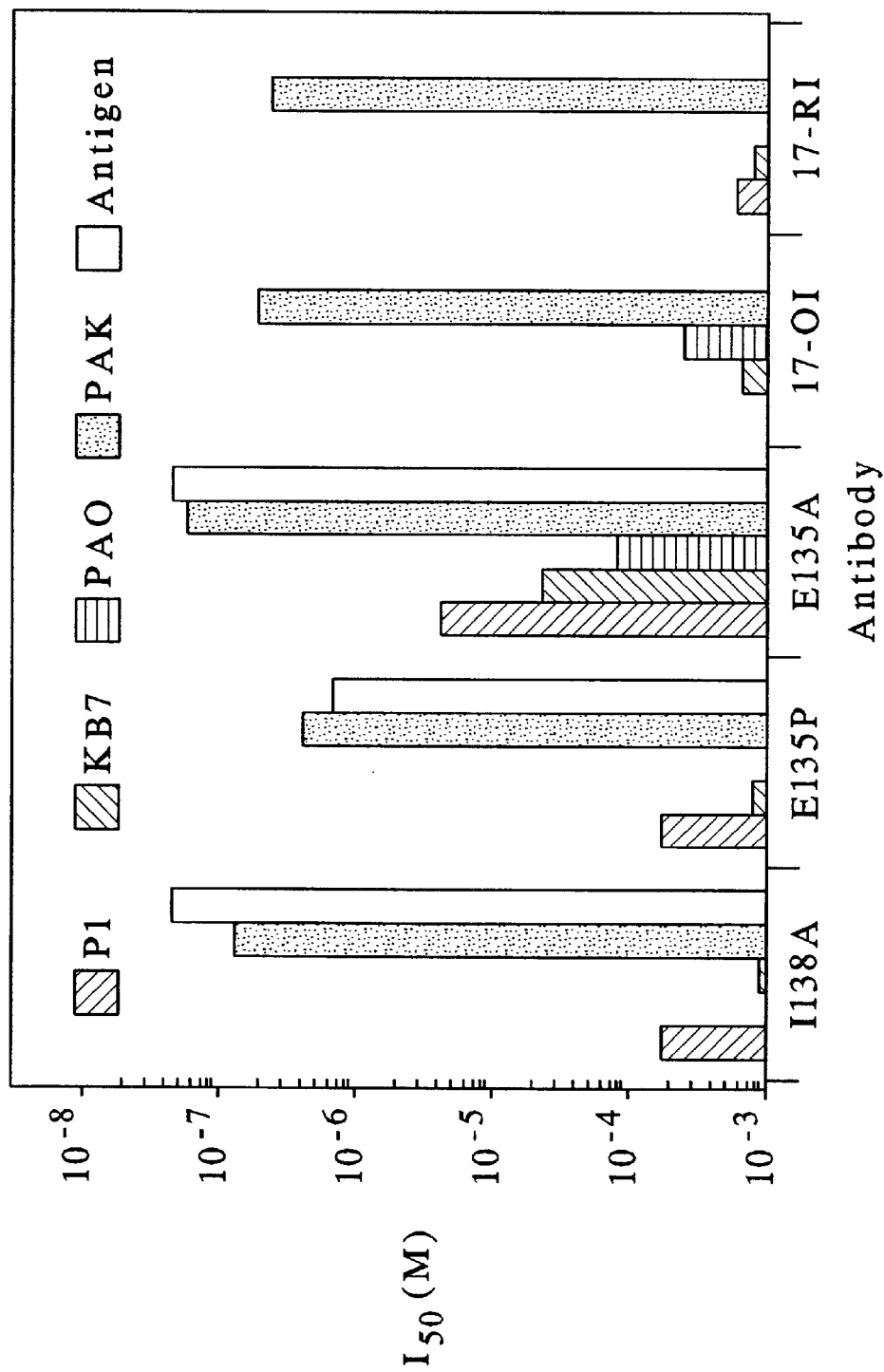
FIG. 12 are competition ELISA plots of the native peptides (PAK, PAO, KB7 and P1) required to achieve 50% inhibition of antibody binding to PAK pili in the presence of antisera 17-R1, 17-O1, E135A, E135P and I138A, where the open columns represent the peptide antigens (I138A, E135P and E135A) to which the antisera I138A, E135P and E135A were generated.

In this analysis, the cross-reactivity of five antisera was studied on microtiter plates coated with native PAK strain pili (Table 2). Competition assays were performed using synthetic peptides specifically representing the homologous C-terminal regions of each of four P. aeruginosa strains AcPAK(128–144)OH, AcPAO(128–144)OH, AcKB7 (128–144)OH and AcP1(126–148)OH) or the corresponding analogs of AcPAK(128–144)OH. By plotting the I50 values of the four strain specific synthetic peptides (strains PAK, PAO, KB7 and P1) and the analogs in separate competition assays with the antisera (FIG. 12 and Table 2), the cross-reactivity of the antisera to the different strains is evaluated. Assays included the native PAK pilin sequence AcPAK (128–144)OH as a control. Antisera E135P, I138A and E135A were all generated to synthetic peptide antigens.

Examination of the results from antisera 17-R1 and 17-O1 indicates that formation of the disulfide bridge between residues 129 and 142 decreases the $K_{PAK}/K_{PAO}$ ratio and therefore is important for cross-reactivity to PAO strain (Table 1; $K_{PAK}/K_{PAO}=4,400$ and 1,270, respectively). Examination of the $I_{50}$ values of 17-O1 and 17-R1 (Table 2) shows that these two antisera have similar affinities for PAK (0.19 and 0.23 $10^{-6}$ M, respectively) while the affinity of antiserum 17-O1 is 4-fold higher for PAO (241 and 1,014 $10^{-6}$ M, respectively).

Cross-reactivity to PAO was also examined in the other antisera: E135A, I138A and E135P. The results shown in Tables 1 and 2 demonstrate that antiserum E135A is cross-reactive to PAK and PAO and the magnitude of this cross-reactivity is equivalent to that of 17-O1 ($K_{PAK}/K_{PAO}$=1,350). However, the $I_{50}$ values (FIG. 12 and Table 2) of both peptides, PAK and PAO, for antiserum E135A increased by a factor of 3-fold over that of antiserum 17-O1 ($I_{50}$; PAK, 0.06 vs 0.19 $10^{-6}$ M; PAO, 81 vs 241 $10^{-6}$ M, respectively). Antiserum I138A was also analyzed for cross-reactivity to PAK and PAO. The affinity for PAK remained similar to that of 17-O1 (Table 2, $I_{50}$; 0.13 vs 0.19 $10^{-6}$ M for I138A and 17-O1, respectively) while that of PAO is reduced about 4-fold (Table 2, $I_{50}$; 909 vs 241 $10^{-6}$ M for I138A and 17-O1, respectively). Therefore, antiserum I138A is about 6-fold less cross-reactive than 17-O1 (Table 1; $K_{PAK}/K_{PAO}$= 7000 vs 1,270).

A proline residue occupies position 135 of the native PAO sequence (FIG. 1). Since position 135 in the native PAK sequence was not critical to PAK/PAO cross-reactivity (Table 1; columns 17-O1 and E135A; row $K_{PAK}/K_{PAO}$=1, 270 vs 1,350, respectively) we reasoned that an immunogen containing an E135P substitution in the native PAK sequence (AcPAK(128–144)OH) might generate antiserum with an enhanced cross-reactivity to PAO. Peptide E135P was synthesized, antiserum was generated in rabbits and cross-reactivity to PAK and PAO was evaluated as before. The results show (Table 2 and FIG. 12) that the affinity for PAK has decreased by about a factor of 2 (0.41 vs 0.19 $10^{-6}$M for E135P and 17-O1, respectively) and the affinity for PAO has decreased approximately 20-fold compared to antiserum 17-O1 (4,751 vs 241 $10_{-6}$ M for E135P and 17-O1, respectively). These results show that the proline substitution at position 135 in the native PAK sequence has significantly decreased the affinity of the homologous antiserum (E135P) for the native PAO sequence which in turn has greatly decreased the antiserum's cross-reactivity (Table 1, $K_{PAK}/K_{PAO}$=11,600 vs 1,270) rather than increased it. In effect, the substitution of proline in the native PAK sequence at position 135 has resulted in the production of antiserum which is highly specific for native PAK peptide in the presence of native PAO peptide while the affinity for native PAK peptide has been lowered by approximately 2-fold (Table 2; row E135P; columns PAK and PAO).

The cross-reactivities to native peptide sequences KB7 and P1 were also studied in all the antisera. A summary of the results is found in FIG. 12 and Table 2. These data show that, although 17-O1 does exhibit cross-reactivity to native PAO sequence, the antisera 17-R1 and 17-O1 do not exhibit broad cross-reactivity as judged by their affinities for the other heterologous peptides from strains P1 and KB7. In addition, antisera I138A, E135A and E135P were examined for their affinity for their respective immunogens (Table 2; column, Antigen $I_{50}$). In each case the antisera demonstrate high affinity and cross-reactivity for both the native PAK sequence and the analogs used to generate the antisera (Table 2 and FIG. 12). As for cross-reactivity to the heterologous strains, PAO, P1 and KB7, only antiserum E135A exhibits broad cross-reactivity with $I_{50}$ values in the range 10-5M to 10-8M (0.06, 81, 22 and 4 $10^{-6}$ M for PAK, PAO, KB7 and P1, respectively, FIG. 12 and Table 2). Not only is the antiserum cross-reactive but this cross-reactivity is significantly enhanced to peptides from strains KB7 and P1 in comparison to the native antiserum 17-O1 and to all the other antisera tested. For example, the affinity of antiserum E135A for peptides PAK and PAO has increased 3-fold and for peptides KB7 and P1, 32 and 300-fold, respectively, compared to antiserum 17-O1. In addition, the data in Table 2 also demonstrates, the affinity of antiserum E135A is from 2- to 7-fold higher than the other antisera for PAK peptide (ratios of $I_{50}$ values), 3- to 59-fold higher for PAO peptide, 32- to 60-fold higher for KB7 peptide and 44- to 300-fold higher in affinity for P1 peptide. In FIG. 12, this is reflected in the histogram of $I_{50}$ values (log10 of the molar concentration of peptide required to achieve 50% inhibition of antiserum E135A binding to PAK pilin) reported for E135A antiserum.

As for the antisera I138A and E135P, the data shows that they are not able to effectively bind heterologous peptides PAO and KB7. However, all three antisera, I138A, E135P and E135A, demonstrate affinity for native peptide sequence P1 which is 7- to 300-fold better than antiserum 17-O1 (176 $10^{-6}$ M for I138A and E135P and 4 $10^{-6}$ M for E135A compared to 1,217 $10_{-6}$ M for 17-O1, FIG. 12 and Table 2). This is surprising since peptide sequence P1 is very different from the sequences of PAK, PAO and KB7 (FIG. 1) in length, amino acid composition and size of the disulfide loop.

In order to test the efficacy of E135A, this peptide was conjugated to tetanus toxoid and the conjugate was used in our A.BY/SnJ mouse model to test active immunization. The A.BY/SnJ mice are less resistant to *P. aeruginosa* infection than normal laboratory mice. It is therefore unnecessary to use immunosuppressive procedures to demonstrate antibody-induced protection. Since antisera E135A was least cross-reactive to PAO strain ($I_{50}$, 0.06 $10^{-6}$ M for PAK vs 81 $10^{-6}$ M for PAO; $K_{PAK}/K_{PAO}$=1,350) compared to the other strains (Table 2), it was important to demonstrate the this level of cross-reactivity could still offer protection to challenge from strain PAO. FIG. 2 demonstrates that challenge with $2\times10^{6}$ cfu (~3 $LD_{50}$; PAO strain) results in protection against lethal challenge. As the plot of survivors vs hours after challenge shows, the two groups of mice (10 mice per group) that were immunized with E135A conjugate or PAO conjugate demonstrated increased survival times when compared with those groups which had been immunized with PAK conjugate or the adjuvant alone as a control. This result demonstrated the enhanced efficacy of this peptide, E135A, over the corresponding PAK native sequence. The result is even more important since examination of the two sequences, PAO and E135A, shows that these sequences differ at 7 positions. The results demonstrate that the replacement of E135 by alanine has created an immunogen which is, for all but one residue, identical to the PAK native sequence—a sequence which does not provide protection against PAO challenge—yet this new sequence is providing protection similar to that of the native PAO sequence.

Mapping studies were used to define specific residues responsible for peptide binding to the antisera. The cross-reactive native polyclonal antisera described here, 17-O1, binds to both PAK and PAO native peptides. Examination of the mapping results for antiserum 17-O1 (Table 1; D134, Q136 and F137; $K_N/K_S$ values) reveals that D134, Q136, and F137 are all critical residues for binding to the native protein.

Antisera was raised to a peptide analog in which E135 was replaced by an alanine at position 135 in native PAK sequence, AcPAK(128–144)OH. This substitution resulted in a large decrease in the contribution to binding from Q136 (6-fold). The contributions from F137 and D134 side-chains have remained large while contributions from residues Q133, I138, and P139 were all significantly enhanced (6- to 450-fold) by this substitution. Cross-reactivity of antiserum E135A to PAO remained the same as with antiserum 17-O1.

The antisera I138A and E135P show some of the most dramatic effects on substitution. In antiserum I138A, the loss of the hydrophobic contribution at I138, by substitution with alanine, has substantially increased the importance of Q133 ($K_N/K_S$=250,000) but cross-reactivity to PAO sequence decreases by a factor of 6-fold over that of antiserum 17-O1. Antiserum E135P demonstrates effects in both the contributing residues and cross-reactivity. This antiserum was generated by substitution of E135, in the PAK native sequence, by the proline residue from position 135 in the PAO native sequence (FIG. 1). The rationale behind this substitution was based on the hypothesis that a more cross-reactive antibody response is generated by using a peptide immunogen in which a side-chain unimportant for PAK strain specificity could be replaced by a side-chain from a different strain that would enhance cross-reactivity to that strain. The mapping results for antiserum E135P show that the critical residues for protein recognition are Q136 and K140 with contributions from D134 and I138. This is a significant shift from the results obtained using antisera 17-O1. With respect to cross-reactivity, antiserum E135P is very specific for strain PAK (Table 1; $K_{PAK}/K_{PAO}$=11,600). The value of $I_{50}$ for PAO (FIG. 12 and Table 2; column PAO; 4,751 $10^{-6}$ M) indicates that native PAO peptide binds very weakly while PAK peptide binding is similar to that of antiserum 17-O1 (FIG. 12 and Table 2; column PAK; 0.41 $10^{-6}$ M). An even more specific example of a side-chain effect on contributions to binding can be demonstrated with antisera which were raised in response to single alanine substitution analogs Q136A and F137A. These antisera failed to bind to the native pili indicating that these two residues are essential for immunogenicity and recognition of the native pilin epitope sequence [42, 43]. Based on the evidence cited here it would be reasonable to suggest that there are both peptide backbone structural features and amino acid side-chain characteristics which, in combination, determine immunogenicity and binding to antisera.

Figure 8:
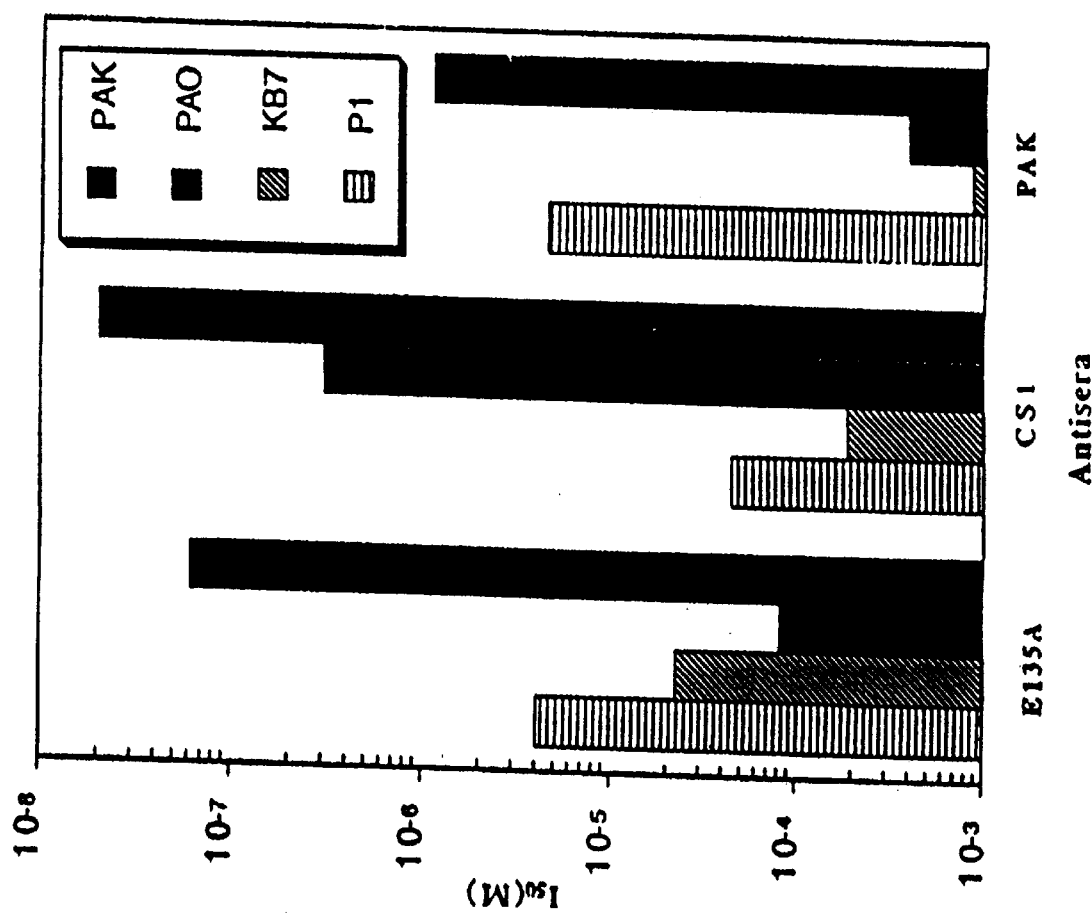
FIG. 8 are competition ELISA plots of the native peptides (PAK, PAO, KB7 and P1) required to achieve 50% inhibition of antibody binding to PAK pili in the presence of antisera E135A, CS1, and PAK, where the column represent the peptide antigens (E135A, CS1, and PAK) to which the antisera were generated.

Similar studies were carried out using antisera against the E135A, CS1, and PAK peptide in reaction with PAK, PAO, KB7, and P1, as indicated in FIG. 8. In addition to the results previously reported for cross-reactivity with the E135A antigen, the CS1 antigen is seen to give very high cross-reactivities with PAK and PAO, and moderate cross-reactivities with KB7 and P1. As seen from the data in FIGS. 4 and 6, CS1 was effective in protecting the subject animal against both P1 and KB7 infection.

Two-dimensional 1H NMR spectroscopy was used to determine the antigenic determinants recognized by the *Pseudomonas aeruginosa* cross-reactive monoclonal antibody PAK-13. The results demonstrated that residues for which spectral changes were observed upon antibody binding were different for each of the peptides. However, these residues are confined to common structural features that comprise each peptide antigen, namely, two β-turns and a hydrophobic pocket.

The examples illustrate the invention, but are in no way intended to limit it.

Unless otherwise stated all reagents were reagent grade. Bovine serum albumin was purchased from Sigma Chemical Co., St Louis, Mo. Goat anti-mouse IgG horseradish peroxidase conjugate was purchased from Jackson Inmunoresearch Laboratories, Inc., West Grove, Pa. 2,2'-azino-di-(3-ethylbenzthiazoline sulfonic acid) was purchased from Boehringer Mannheim, Laval, PQ. Untreated polystyrene 96-well flat bottom microtiter plates were purchased from Costar Corp., Cambridge, Mass. Freund's complete and incomplete adjuvants were purchased from GIBCO Laboratories, Life Technologies Inc.,Grand Island, N.Y. Keyhole limpet haemocyanin was purchased from Sigma Chemical Company, St. Louis, Mo. and tetanus toxoid was purchased from Pasteur Merieux Connaught Laboratories, North York, ON, Canada. Adjuvax adjuvant was purchased from Alpha-Beta Technology, One Innovation Drive, Worcester, Mass.

EXAMPLE 1

Bacterial Pili

The bacterial pili employed in this study were obtained from the *P. aeruginosa* strain PAK/2pfs. Purification of the pili was as previously described [47].

The synthetic pilin peptides and their analogs were prepared following the general procedure for solid-phase peptide synthesis (SPPS) as described by Erickson and Merrifield [48] and the SPPS protocols, purification, and characterization of the peptides have been described [44].

The preparation of peptide conjugates has been described by Lee et al. [6]. Peptides containing the photo reactive group, benzoyl benzoic acid, attached to the N-terminal end were conjugated to the protein carrier, keyhole limpet haemocyanin (KLH). The peptides (2–5 mg) dissolved in 10–20 µl of water were mixed with 500 µl of 8M urea containing KLH (10 mg). This solution was then irradiated at 350 nm for one hour at 48° C. in a RPR 208 preparative reactor (Rayonet, The Southern New England Ultraviolet Co., Middletown, Conn.) equipped with RPR 350 nm lamps. Unconjugated peptides were removed by successive dialysis against 8M urea, 1M urea, PBS at pH 7.2. The product was lyophilized and the peptide incorporation determined by amino acid analysis.

Peptides containing the photo reactive group, benzoyl benzoic acid, attached to the N-terminal end were conjugated to the protein carrier, tetanus toxoid (TT). The peptides (2–5 mg) dissolved in 10–20 µl of water were mixed with 500 µl PBS at pH 7.2 containing TT (10 mg). This solution was then irradiated at 350 nm for one hour at 48° C. in a RPR 208 preparative reactor (Rayonet, The Southern New England Ultraviolet Co., Middletown, Conn.) equipped with RPR 350 nm lamps. Unconjugated peptides were removed by dialysis against PBS at pH 7.2. The product was lyophilized and the peptide incorporation determined by amino acid analysis.

EXAMPLE 2

Antipeptide Antisera

A group of 3 New Zealand White rabbits were used for immunization in a peptide conjugate experiment. The rabbits were used at eight weeks of age and at approximately 2 kilograms in weight. Prior to immunization, a small sample of blood (5 ml) was drawn from the vein of the rabbit's ear and used as preimmune sera. The peptide-KLH conjugates were dissolved in sterile PBS and mixed with equal volume of Freund's complete adjuvant. This mixture was then thoroughly mixed until a thick white emulsion formed. A two-site (subcutaneous and intramuscular) injection with 200 µl/site of the emulsion was performed on each rabbit. The amount of peptide-conjugate injected was 200 to 350 µg/rabbit, depending on the degree of incorporation of the peptide analog on KLH. Two booster injections were administered at two week intervals using the same amount of the peptide conjugate emulsified with Freund's incomplete adjuvant. Blood samples (5 ml each) were taken 10 days after the third injection. The antiserum titer was then determined by direct ELISA. Further booster injections and sera collections were subsequently performed at 4 week intervals.

EXAMPLE 3

Active Immunization with Peptide Conjugate

A.BY/SnJ mice were actively immunized at week 0 with 40–50 μg or peptide-tetanus toxoid conjugate mixed with 100 μg of ADJUVAX as adjuvant in 50 ul of 10 mM PBS at pH 7.2. Control mice were given 50 μl of 10 mM PBS at pH 7.2 containing 100 μg of ADJUVAX. The mice were then boosted at weeks 2 and 4 and challenged with $2 \times 10^5$ cfu of *P. aeruginosa* strain PAO ($\sim 3 \times LD_{50}$) at week 6. Each test group and the control group consisted of ten animals. The effectiveness of the vaccine was determined by the survival rate of the test animals up to 48 hours.

EXAMPLE 4

Enzyme-linked Immunosorbent Assay (ELISA)

Competitive ELISAs were performed according to the following protocol. Untreated 96-well flat bottom microtiter plates were coated with 0.2 μg/well of PAK pili for 1 hour at 37° C. and blocked with 5% (wt/vol) BSA (100 μl/well) dissolved in 10 mM PBS, pH 7.4, containing 150 mM sodium chloride for 8 hours at 4° C. The plates were then washed, five times, with 10 mM PBS, pH 7.4, containing 150 mM sodium chloride and 0.05% (w/v) BSA (buffer A). Raw sera containing polyclonal antibodies (dilution, 1:5,000) were preincubated with equal volumes of serially diluted epitopic peptide pilin sequences for 1 hour at 37° C. These solutions were added (100 μl/well) to the pili coated wells on the microtiter plate. Following incubation for 2 hours at 37° C., the plates were washed, five times, with buffer A. A goat anti-rabbit IgG horseradish peroxidase conjugate, that had been diluted 1:5000 with buffer A, was added to the wells (100 μl/well). A second incubation was performed for 2 hours at 37° C. and the plates were washed, five times, with buffer A. 2,2'-azino-di-(3-ethylbenzthiazoline sulfonic acid) (ABTS) (1 mM) in 10 mM sodium citrate buffer, pH 4.2, containing 0.03% (v/v) hydrogen peroxide was used for detection. Finally, the absorbance at 405 nm was determined by using a Titertek Multiskan Plus MK II microplate reader (Flow Lab Inc., Mclean, Va).

The percentage inhibition (%Inhibition) for each competitive assay was calculated by the following formula:

%Inhibition=100%−[(A405 Competition/A405 No Competition)*100%]

The percent inhibition at each peptide concentration was determined from the mean value of 8 repetitions. The competitive binding profile was plotted as %Inhibition (±SD) vs Log 10(competitor concentration). The $I_{50}$ value (competitor concentration that causes 50% inhibition) was determined by using the software KaleidaGraph (Synergy Software, Reading, Pa). The apparent association constant (Ka) of the antiserum for each peptide analogue can be calculated by the formula $Ka=(I_{50})-1$ as described by Nieto et al. [49].

TABLE 1

Epitope Mapping of Five Anti-PAK Peptide Antibodies $K_N/K_S$[a] Ratios of the Antipeptide Antibodies

| Peptide[b] | 17-R1 | 17-01 | E135A | I138A | E135P |
|---|---|---|---|---|---|
| K128A | 1 | 1 | <1 | — | — |
| C129 | — | — | — | — | — |
| T130A | 2 | 1 | <1 | — | — |
| S131A | 2 | 1 | <1 | — | — |
| D132A | 10 | 6 | 1 | <1 | <1 |
| Q133A | 9 | 20 | 830 | >250,000 | <1 |
| D134A | 10 | 1,600 | 1,200 | 71 | 267 |
| E135A | 480 | 2 | 1 | 3 | 3 |
| Q136A | 390 | 3,200 | 520 | 60 | >10,000 |
| F137A | >10,000 | >10,000 | >4,800 | <1 | 20 |
| I138A | 18 | 1 | 450 | <1 | 208 |
| P139A | 280 | 14 | 390 | <1 | 1 |
| K140A | 2 | 2 | 8 | 120 | >100,000 |
| G141A | 1 | 1 | 1 | — | — |
| C142 | — | — | — | — | — |
| S143A | 1 | <1 | 1 | — | — |
| K144A | 1 | 1 | 1 | — | — |
| $K_{PAK}/K_{PAO}$[c] | 4,400 | 1,270 | 1,350 | 7,000 | 11,600 |

[a]The values of the apparent binding constants (Ka) are expressed as $K_N$ for native peptide PAK and $K_S$ for the corresponding analogue being tested. Values for $K_N/K_S$ ratios that are >1,000 are boxed and the side-chain at this position is considered critical for antibody binding.

[b]PEPTIDE designates the native sequence of PAK pilin peptide and the residue within this sequence which has been substituted by alanine. The cysteines (129 and 142) are retained for the purposes of disulfide bridge formation. There are 15 single alanine substitution analogues each designated by the position of substitution. For example, K12SA represents position Lys 128 substituted by Ala.

[c]Cross-reactivity of an antiserum is expressed as the ratio $K_{PAK}/K_{PAO}$. A value of 1 would indicate that the antiserum has the same affinity for native PAO peptide sequence as it does for native PAK peptide sequence in competition ELISA assay and therefore has excellent cross-reactivity. The larger the value of $K_{PAK}/K_{PAO}$ the more specific the antiserum is for PAK native sequence and the less cross-reactive it is with the native PAO sequence.

TABLE 2

Antisera Affinity Results

| | Antigen[b] | Peptide Competitor[c] | | | | | | | |
|---|---|---|---|---|---|---|---|---|---|
| | | PAK | | PAO | | KB7 | | P1 | |
| Anti-serum[a] | $I_{50}$ (μM) | $I_{50}$[d] (μM) | A[e] | $I_{50}$ (μM) | A | $I_{50}$ (μM) | A | $I_{50}$ (μM) | A |
| I138A | 0.05 | 0.13 | +1.5 | 909 | −3.8 | 1,320 | −1.9 | 176 | +6.9 |
| E135P | 0.70 | 0.41 | −2.2 | 4,751 | −19.7 | 835 | −1.2 | 176 | +6.9 |

TABLE 2-continued

Antisera Affinity Results

| | | Peptide Competitor[c] | | | | | | | |
|---|---|---|---|---|---|---|---|---|---|
| | Antigen[b] | PAK | | PAO | | KB7 | | P1 | |
| Anti-serum[a] | $I_{50}$ ($\mu$M) | $I_{50}$[d] ($\mu$M) | A[e] | $I_{50}$ ($\mu$M) | A | $I_{50}$ ($\mu$M) | A | $I_{50}$ ($\mu$M) | A |
| E135A | 0.05 | 0.06 | +3.2 | 81 | +3.0 | 22 | +32.0 | 4 | +304 |
| 17-01 | 0.19 | 0.19 | 1.0 | 241 | 1.0 | 704 | 1.0 | 1,217 | 1.0 |
| 17-R1 | — | 0.23 | -1.2 | 1,1014 | -4.2 | 845 | -1.2 | 608 | +2.0 |

[a]Antisera raised to the native PAK peptide sequence 128–144 in the disulfide-bridged (oxidized) form (17-01) and the reduced form (17-R1) and the single substitution analogues of this disulfide-bridged native PAK sequence (I138A, I135P and I135A).
[b]Antigen $I_{50}$ represents the $I_{50}$ value of the corresponding disulfide-bridged peptide analogue that was used to raise antiserum I138A, I135P and I135A or the disulfide-bridged native PAK sequence and reduced native PAK sequence used to raise antiserum 17-01 and 17-R1, respectively.
[c]Peptide competitors in the ELISA assays were the oxidized (disulfide-bridged) peptides of the receptor binding domains of pilin strains PAK, PAO, KB7 and P1 (FIG. 1).
[d]The $I_{50}$ values indicate the concentration of peptide required to produced 50% inhibition of antibody binding to PAK pilin.
[e]"A" represents an increase or decrease in the affinity of the antiserum against a particular native sequence (PAK, PAO, KB7 and P1) compared to the affinity of the antiserum of native PAK (17-01). A positive value is the number fold improvement in affinity whereas a negative value represents the number fold decrease in affinity of the antiserum for that particular native sequence compared to native PAK antiserum 17-01.

SEQUENCE LISTING

<160> NUMBER OF SEQ ID NOS: 15

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Lys Cys Thr Ser Asp Gln Asp Glu Gln Phe Ile Pro Lys Gly Cys Ser
 1               5                  10                  15

Lys

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide

<400> SEQUENCE: 2

Ala Cys Lys Ser Thr Gln Asp Pro Met Phe Thr Pro Lys Gly Cys Asp
 1               5                  10                  15

Asn

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Lys Cys Lys Ser Asp Gln Asp Pro Gln Phe Ile Pro Lys Gly Cys Ser
 1               5                  10                  15

Lys

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Lys Cys Thr Ser Thr Gln Asp Pro Gln Phe Ile Pro Lys Gly Cys Ser
 1               5                  10                  15

Lys

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

Lys Cys Thr Ser Thr Gln Asp Pro Gln Phe Thr Pro Lys Gly Cys Ser
 1               5                  10                  15

Lys

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Lys Cys Lys Ser Thr Gln Asp Glu Met Phe Thr Pro Lys Gly Cys Ser
 1               5                  10                  15

Lys

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide

<400> SEQUENCE: 7

Lys Cys Thr Ser Asp Gln Asp Ala Gln Phe Ile Pro Lys Gly Cys Ser
 1               5                  10                  15

Lys

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Lys Cys Thr Ser Asp Gln Asp Pro Gln Phe Ile Pro Lys Gly Cys Ser
 1               5                  10                  15

Lys

```
<210> SEQ ID NO 9
<211> LENGTH: 14
<212> TYPE: PRT
<213> ORGANISM: Artificial Sequence
<220> FEATURE:
<223> OTHER INFORMATION: Synthetic peptide

<400> SEQUENCE: 9

Cys Thr Ser Thr Gln Glu Glu Met Phe Ile Pro Lys Gly Cys
  1               5                  10

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide

<400> SEQUENCE: 10

Cys Thr Ser Asn Ala Asp Asn Lys Tyr Leu Pro Lys Thr Cys
  1               5                  10

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide

<400> SEQUENCE: 11

Cys Ala Thr Thr Val Asp Ala Lys Phe Arg Pro Lys Gly Cys
  1               5                  10

<210> SEQ ID NO 12
<211> LENGTH: 19
<212> TYPE: PRT
<213> ORGANISM: Artificial Sequence
<220> FEATURE:
<223> OTHER INFORMATION: Synthetic peptide

<400> SEQUENCE: 12

Cys Lys Ile Thr Lys Thr Pro Thr Ala Trp Lys Pro Asn Tyr Ala Pro
  1               5                  10                  15

Ala Asn Cys

<210> SEQ ID NO 13
<211> LENGTH: 19
<212> TYPE: PRT
<213> ORGANISM: Artificial Sequence
<220> FEATURE:
<223> OTHER INFORMATION: Synthetic peptide

<400> SEQUENCE: 13

Cys Gly Ile Thr Gly Ser Pro Thr Asn Trp Lys Ala Asn Tyr Ala Pro
  1               5                  10                  15

Ala Asn Cys

<210> SEQ ID NO 14
<211> LENGTH: 19
<212> TYPE: PRT
<213> ORGANISM: Artificial Sequence
<220> FEATURE:
<223> OTHER INFORMATION: Synthetic peptide
```

```
<400> SEQUENCE: 14

Cys Ser Ile Ser Ser Thr Pro Ala Asn Trp Lys Pro Asn Tyr Ala Pro
1               5                   10                  15

Ser Asn Cys

<210> SEQ ID NO 15
<211> LENGTH: 17
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (3)...(3)
<223> OTHER INFORMATION: Xaa = Thr, Lys, or Ala
<221> NAME/KEY: VARIANT
<222> LOCATION: (5)...(5)
<223> OTHER INFORMATION: Xaa = Asp, Thr, or Asn
<221> NAME/KEY: VARIANT
<222> LOCATION: (6)...(6)
<223> OTHER INFORMATION: Xaa = Gln, Ala, or Val
<221> NAME/KEY: VARIANT
<222> LOCATION: (8)...(8)
<223> OTHER INFORMATION: Xaa = Glu, Pro, Asn, or Ala
<221> NAME/KEY: VARIANT
<222> LOCATION: (9)...(9)
<223> OTHER INFORMATION: Xaa = Gln, Met, or Lys
<221> NAME/KEY: VARIANT
<222> LOCATION: (11)...(11)
<223> OTHER INFORMATION: Xaa = Ile, Thr, Leu, or Arg

<400> SEQUENCE: 15 ys Cys Xaa Ser Xaa Xaa Asp Xaa Xaa Phe Xaa Pro Lys Gly Cys Ser
1               5                   10                  15 ys
```

It is claimed:

1. A peptide vaccine for immunizing or treating a patient against infection by *Pseudomonas aeruginosa*, comprising (i) a peptide identified as SEQ ID NO. 3; and
(ii) a carrier protein conjugated to the peptide.

* * * * *